United States Patent [19]

Ayer et al.

[11] Patent Number: 4,755,180
[45] Date of Patent: Jul. 5, 1988

[54] DOSAGE FORM COMPRISING SOLUBILITY REGULATING MEMBER

[75] Inventors: Atul D. Ayer, Mt. View; Patrick S. L. Wong, Hayward, both of Calif.

[73] Assignee: Alza Corporation, Palo Alto, Calif.

[21] Appl. No.: 874,961

[22] Filed: Jun. 16, 1986

[51] Int. Cl.[4] .................. A61K 9/22; A01N 25/12; A61J 3/00; A61J 3/10

[52] U.S. Cl. .................. 604/892.1; 424/465; 424/469; 424/473

[58] Field of Search .................. 424/14–22, 424/422–424, 427, 430, 451–453, 455, 457, 458, 460, 461, 462, 468, 473, 477, 479; 604/890–893, 896, 797

[56] References Cited

U.S. PATENT DOCUMENTS

| 1,815,902 | 7/1931 | Ellzey | 424/453 |
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 604/893 |
| 4,200,098 | 4/1980 | Ayer et al. | 128/260 |
| 4,235,236 | 11/1980 | Theeuwes | 128/260 |
| 4,320,759 | 3/1982 | Theeuwes | 604/892 |
| 4,379,454 | 4/1983 | Campbell et al. | 128/156 |
| 4,553,973 | 11/1985 | Edgren | 604/890 |
| 4,610,686 | 9/1986 | Ayer et al. | 604/892 |

FOREIGN PATENT DOCUMENTS

| 2524311 | 10/1983 | France | 424/453 |
| 8303061 | 9/1983 | PCT Int'l Appl. | 424/452 |

Primary Examiner—C. Fred Rosenbaum
Assistant Examiner—Sharon Rose
Attorney, Agent, or Firm—Paul L. Sabatine; Edward L. Mandell; Shelley G. Precivale

[57] ABSTRACT

An osmotic dosage form is disclosed comprising a polymeric olefin, vinyl, condensation, addition or silicon film that surrounds a member selected from the group consisting of a buffer and osmogent which member is released by the film as a means for governing the solubility of a beneficial agent in the dosage form.

5 Claims, 3 Drawing Sheets

FLOW PROCESS

DOSAGE FORM COMPRISING SOLUBILITY REGULATING MEMBER

CROSS-REFERENCE TO RELATED COPENDING APPLICATION

This application is copending with an application identified by attorney docket number ARC 1263 now U.S. Ser. No. 06/876,138 filed June 19, 1986.

FIELD OF THE INVENTION

This invention pertains to both a novel and useful dosage form. More particularly, the invention relates to a dosage form comprising a beneficial agent and a member comprising a beneficial agent and a member comprising a polymeric-composition-coated around an osmotically effective solute used for regulating the solubility of the beneficial agent.

BACKGROUND OF THE INVENTION

Dosage forms made in the form of an osmotic delivery system are known to the delivery art in U.S. Pat. Nos. 3,845,770 and 3,916,899, both issued to patentees Felix Theeuwes and Takeru Higuchi. The dosage form disclosed and claimed in these patents comprise a semipermeable wall that surrounds a compartment containing a beneficial agent, usually a beneficial drug.

The wall is permeable to the passage of an external fluid and substantially impermeable to the passage of a beneficial drug. There is at least one passageway through the wall for delivering the beneficial agent from the dosage form. The dosage form releases the beneficial agent by fluid being continuously imbibed through the wall into the dosage form at a rate determined by the permeability of the semipermeable wall and the osmotic pressure gradient across the wall. This physical-chemical action produces a solution containing the beneficial agent that is hydrodynamically dispensed through the passageway from the dosage form.

The above described patents also are useful for delivering a beneficial agent that exhibits a low solubility, or exhibits a high solubility in an external fluid imbibed into the dosage form. The dosage form delivers such beneficial agent by blending the beneficial agent with an osmotically—effective solute, known also as osmagent. The osmagent in the dosage form are a substantial motive force as they exhibit an osmotic pressure gradient across the wall of the dosage form, and they imbibe fluid into the dosage form. The osmagent produces a solution with the imbibed fluid that is osmotically delivered from the dosage form concomitantly transporting therewith undissolved, or dissolved beneficial agent form the dosage form.

The dosage form of these patents is an outstanding invention and its represents a pioneer advancement in the delivery art, and it is endowed with ideal delivery kinetics useful for delivering these beneficial agents. Now, it has unexpectedly been discovered there is an occasional instance where the delivery kinetics of the dosage form can be improved leading to even more desirable results. For example, when a beneficial agent exhibits a low or a high solubility and is mixed with an osmagent to produce an equilibrium ratio, the resulting beneficial agent solubility in the presence of all of the osmagent often is too small, usually less than 50 mg/ml, or to high, usually greater than 400 mg/ml, for rendering this blend dispensable at a controlled rate over a prolonged period of time. When the resulting beneficial agent's solubility is low, it is difficult to deliver the beneficial agent at meaningful therapeutic rates; and, when the resulting beneficial agent's solubility is to high it is delivered from the dosage form in a premature period of time.

Thus, in the light of the above discussion, it will be readily appreciated by those versed in the subject art that a critical need exists for a dosage form for delivering a beneficial agent that exhibits a hard to delivery solubility, especially where the dosage form overcomes the tribulations associated with the prior art. Likewise, it will be further appreciated by those skilled in the art, that if a novel and useful dosage form is made available for delivering these beneficial agents, such a dosage form have a positive value and also represent a substantial contribution to the dispensing art.

OBJECTS OF THE INVENTION

Accordingly, in view of the above presentation, it is an immediate object of this invention to provide a novel and useful dosage form that overcomes the difficulties known to the prior art.

Another object of the present invention is to provide a dosage form comprising a polymeric-coated osmagent for governing the rate of osmagent available for delivering a beneficial agent from a dosage form.

Another object of the present invention is to provide a dosage form for delivering a beneficial agent that exhibits a low or a high solubility in aqueous fluids but can be delivered by the dosage form through its ability to provide an osmagent at a controlled rate over time.

Another object of the present invention is to provide a dosage form for delivering a beneficial agent that exhibits a low or a high solubility in aqueous fluids can be delivered by the dosage form through its ability to provide an osmagent at a controlled rate over time.

Another object of the present invention is to provide a dosage form manufactured as an osmotic dispensing device, which dosage form comprises means for providing an osmagent at a controlled rate for delivering a beneficial agent at a correspondingly controlled rate.

Another object of the present invention is to provide a dosage form manufactured as an osmotic dispensing device, which dosage form comprises a film comprising a polymeric composition that surrounds an osmagent for delivering the osmagent at a controlled rate useful for delivering a beneficial drug as a complete pharmaceutical regimen to a warm-blooded animal for a particular time period, the use of which requires intervention only for irritation and optional termination of the regimen.

Another object of the invention is to provide a polymeric formulation that surrounds an osmotically-effective solute that is released by the polymeric formulation for aiding in delivering a beneficial agent from a dosage form over a prolonged period of time.

Another object of the present invention is to provide a polymeric film surrounding an osmagent that is released at a controlled rate for controlling the rate of imbibition of fluid into a dosage form, whereby a beneficial drug is delivered at a meaningful rate over a prolonged period of time from the dosage form.

Other objects, features and advantages of the invention will be more apparent to those versed in the dispensing art from a reading of the detailed description of the specification, taken in conjunction with the drawing figures and the accompanying claims.

BRIEF DESCRIPTION OF THE DRAWING FIGURES

In the drawing figures, which are not drawn to scale, but are set forth to illustrate various embodiments of the invention, the drawing figures are as follows.

In the drawing figures and in the specification, like parts in related figures are identified by like numbers. The terms appearing earlier in the specification and in the description of the drawing figures, as well as embodiments thereof, are further described elsewhere in the disclosure.

DETAILED DESCRIPTION OF THE DRAWING FIGURES

Figure 1:
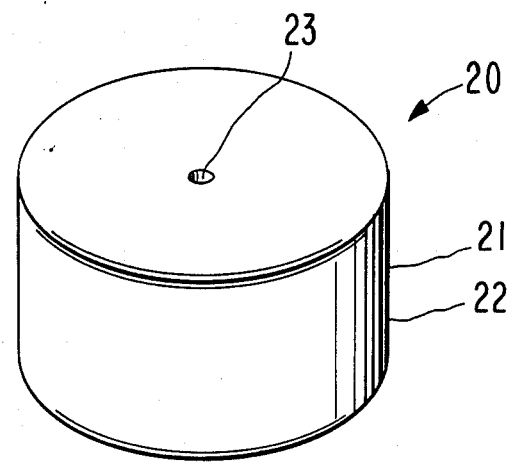
FIG. 1 is a general view of a dosage form provided by the invention, which dosage form is optionally designed and shaped for oral administration of a beneficial drug.

Turning now to the drawing figures in detail, which drawing figures are an example of the dosage form provided by the invention, and which examples are not to be construed as limiting, one example of the dosage form is seen in FIG. 1 and designated by the numeral 20. In FIG. 1, dosage form 20 comprises a body member 21 comprising a wall 22 that surrounds and forms an internal compartment, not seen in FIG. 1. Dosage form 20 further comprises at least one exit means 23 for connecting the exterior of dosage form 20 with the exterior of dosage form 20.

Figure 2:
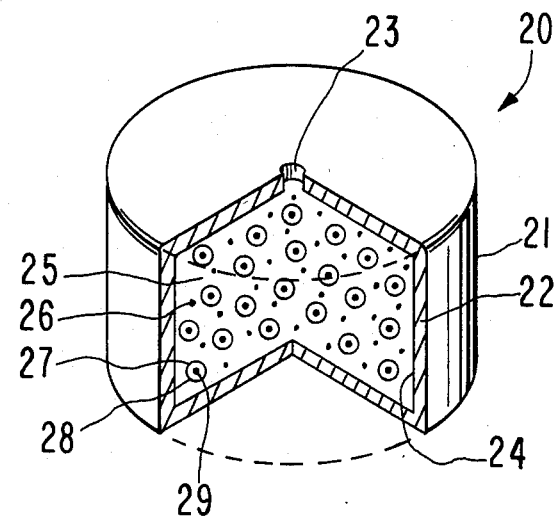
FIG. 2 is a dosage form seen in opened section for illustrating the internal structure of the dosage form; and, FIG. 3 is a dosage form seen in opened section which dosage form comprises a microporous agent releasing surface.

FIG. 2 illustrates dosage form 20 of FIG. 1 comprising body member 21, and wall 22. Wall 22 is opened at 24 for illustrating the structure of dosage form 20. Wall 22 surrounds and defines an internal compartment 25. Wall 22 of dosage form 20 comprises at least a part, or totally, a composition that is permeable to the passage of an exterior fludid present in the environment of use. Wall 22 is substantially impermeable to the passage of a beneficial agent, a drug, and other ingredients present in compartment 25. Wall 22 comprises a polymeric composition that is inert and maintains its physical and chemical integrity during the dispensing life time of dosage form 20. The phrase keeps its physical and chemical integrity is an art accepted phrase that denotes wall 22 does not lose its structure and it does not change during the dispensing life of dosage form 20. Typical materials for forming wall 22 comprise selectively semipermeable polymers known to the art as osmosis and reverse osmosis polymers. These polymeric compositions comprises a member selected from the group consisting of a cellulose ester, cellulose ether, cellulose ester-ether, cellulose acylate, cellulose diacylate, cellulose triacylate, cellulose triacetate. In one presently preferred embodiment, wall 22 is a composition comprising cellulose acetate having an acetyl content of 32%, cellulose acylate having an acetyl content of 39.8%, and cellulose acylate having an acetyl content of 43.3%.

Internal compartment 25 houses a dispensable beneficial agent formulation 26, more preferably a beneficial drug formulation identified by dots. The expression drug formulation 26 as used for the purpose of this invention broadly includes any compound, composition of matter, or mixture thereof, that can be delivered form dosage form 20 to produce a beneficial and useful therapeutic result. The term drug more specifically includes an substance that produces a local or a systemic effect in animals, avians, pisces and reptiles. The term animals includes primates, humans, household, sport, farm and zoo animals, and the like. The drugs that can be delivered by the dosage form of the invention include organic and inorganic drugs the active drug that can be delivered by dosage form 20 include without limitation analgesics, antiparkinson, anti-inflammatory, anesthetics, antimicrobials, anti-malarials, anti-parasites, anti-convulsants, central nervous system acting drugs, depressants, diuretics, hypnotics, sedatives, psychic energizers, tranquilizers, muscle relaxants, muscle contractants, hromones, contraceptives, sympathomimetrics, neoplastics, hypoglycemics, ophthalmics, electrolyte, cardiovascular, and the like.

The amount of drug formulation 26 present in dosage form 20 will vary depending on the therapeutic activity of the drug and the amount of drug to be administered to the recipient. Generally, dosage form 20 will contain from 0.1 mg to 1.250 g or more, with individual dosage forms containing for example 5 mg, 25 mg, 50 mg, 125 mg, 275 mg, 500 mg, and the like. The drug can be in dosage form 20 in various forms such as granules, powders, crystals, and the like. The beneficial drugs, their therapeutic properties and their solubilities are known to the drug dispensing art in *Pharmaceutical Sciences*, by Remington, 15th. Ed., 1975 published by the Mack Publishing Co., Easton, Penna; and in *USAN and the USP Dictionary of Drug Names*, Mary G. Griffiths Ed., 1985, published by USP Convention Inc., Rockville, Md.

Internal compartment 25 additionally houses means 27 for governing the solubility of a drug formulation 26 in fluid imbibed through semipermeable wall 22 into compartment 25. Means 27 consists essentially of an osmagent release rate controlling film 28 that surrounds an confines an osmagent 29. Exemplary of release rate controlling films 28 that can be used for the purpose of this invention, are a member selected from the group consisting essentially of olefin and vinyl-type polymers; condensation-type polymers; addition-type polymers; organo-silicon polymers; and the like. More specifically, the polymeric formulations that can be used for the purpose of this invention include poly(methmethyacrylate); poly(butylmethacrylate); poly(ethylene); ethylene-vinyl acetate copolymer; poly(dimethylsiloxane); poly(urethane); and the like. The rate controlling film releases an osmagent in whose presence a drug exhibiting low solubility has its solubility increased, or the rate controlling film releases an osmagent in whose presence a drug exhibiting high solubility has its solubility decrease in fluid imbibed into compartment 25.

The rate of release of a osmagent 29 through release rate controlling film 28 can be determined by standard procedures. Various techniques such as the transmission method, the sorption method, and the like can be used for measuring permeability. One technique that can be used is to cast, or to hot press a film of the material to a thickness in the range of 1 to 30 mils. The film is used as a barrier between a rapidly stirred, for example, 150 r.p.m., saturated solution of the osmagent and a rapidly stirred solvent bath, both maintained at a constant temperature, usually 37° C. Samples are withdrawn periodically from the solvent bath and analyzed for the osmagent concentration. Then, by plotting osmagent 29 concentration in the solvent bath versus time, the permeability contant P of the film is determined by Fick's First Law of Diffusion as follows:

$$\text{Slope of plot} = \frac{Q_1 - Q_2}{t_1 - t_2} = P\frac{AC}{H}$$

wherein $Q_1$ is the cumulative amount of osmagent 29 in the solvent in micrograms at $t_1$; $Q_2$ is the cumulative amount of osmagent in solvent in micrograms at $t_2$; $t_1$ is the elapsed time to the first sample, i.e. $Q_1$; $t_2$ is the elapsed time in the second sample, i.e. $Q_2$; A is the area of film in cm$^2$; C is the initial concentration of osmagent 29; and H is the thickness of the film in cm. Then, by determining the slope of the plot, and solving the equation using the known or measured values of A, C and H, the permeability P constant in cm$^2$/time of this film for a given osmagent is determined for the purpose of the invention.

The solubility of a drug in fluid imbibed into compartment 25 can be determined by various art known techniques. One method consists in preparing a saturated solution, for example, a fluid plus drug and ascertaining by analyses the amount of drug present in a definite quantity of the fluid. A simple apparatus for this purpose consists of a test tube of medium size fastened upright in a water bath maintained at constant temperature and pressure, for example, 37.5° C. and at one atmosphere. The fluid and the drug are placed in the tube and stirred by means of a motor driven rotating glass spiral. After a given period of stirring, a definite weight of the fluid is analyzed and the stirring continued for an additional period of time. If the analysis shows no increase of dissolved substance after successive periods of stirring, in the presence of excess solid product in the fluid, the solution is saturated and the results are taken as the solubility of the product in the fluid. Numerous other methods are available for the determination of the solubility of a product in a fluid. Typical methods used for the measurement of solubility are chemical analysis, measurements of density, refractive index, electrical conductivity, and the like. For the purpose of this invention an osmagent is used to increase the solubility of a drug when the solubility of the drug is less than 75 mg/ml in the external fluid, for example an aqueous fluid such as water, and an osmagent is used to decrease the solubility of the drug when the solubility of the drug is greater than 400 mg/ml in an aqueous-type fluid. Details of various methods for determining solubilities are described in *United States Public Health Service Bulletin,* No. 67 of the Hygienic Laboratory; *Encyclopedia of Science and Technology,* Vol. 12, pages 542 to 556, 1971, published by McGraw-Hill, Inc., and, *Encyclopedia Dictionary of Physics,* Vol. 6, pages 545 to 577, 1962, published by the Pergamon Press Inc.

Representative of a beneficial drug and an osmagent that can be used for controlling the solubility are benfurodil hemisuccinate a cardiotonic whose solubility is increased in an osmagent that produces an alkaline solution, the diuretic benzthiazide that exhibits a greater solubility in an alkaline environment; the cathartic emodin which exhibits an increased solubility in an alkaline enriontment; the adrenergic p-hydroxy-ephedrine in alkaline pH; the analgesic phenopyrazone in alkaline environment; the diuretic theophylline sodium glycinate increased solubility in alkaline pH of 8.4; the decongestant cafaminol soluble at pH 6.9; the antimalarial chlorguanide pH 5.8–6.3; the antimalarial chloroquine buffered to pH 4.5; the choleretic dehydrocholic acid soluble at pH 7.4 in ethyl acetate; the analgesic p-bromoacetanilide soluble in ethyl acetate; the vasodilator inositol niacinate soluble in acidic pH; the analgesic ketoprofen in ethyl acetate; the psychomimetric lysergic acid in sodium carbonate; the antinauseant methallatal buffered in sodium carbonate; the muscle relaxant pipoxolan hydrochloride at a neutral pH; and the like.

Osmagents, known also as osmotically effective solutes, that can be surrounded with release rate film 28 include a member selected from the group consisting of magnesium sulfate, magnesium chloride, sodium chloride, potassium sulfate, sodium carbonate, sodium sulfite, potassium acid phosphate, urea, sodium acetate, ethyl acetate, and the like. The osmagent can be in various forms such as particles, powders and the like. The pH of a saturated solution of an osmagent is ascertainable with a pH member. The pH of osmagent solution are known in *Handbook of Chemistry and Physics,* 56th. Ed., published by CRC Press.

Figure 3:
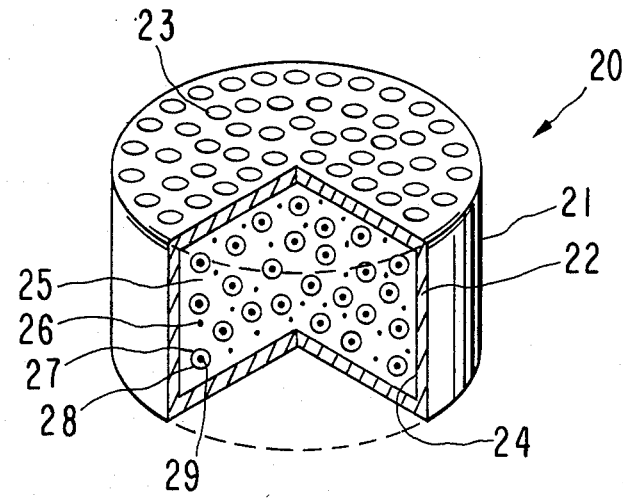

FIG. 3 depicts another dosage form 20 comprises body member 21, wall 22, compartment 25 containing beneficial agent 26 and means 27 which means comprises release rate film 28 surrounding osmagent 29. FIG. 3 also depicts exit means 23. The expression exit means 23 as used herein comprises both means and methods suitable for releasing drug formulation 26 from compartment 25. The expression includes at least one passageway, as seen in FIG. 1, or two or more passageways, with one on each face of dosage form 20. The passageway passes through wall 22 for communicating with compartment 25. The expression passageway includes aperture, orifice, bore, pore, porous element through which a drug can migrate, a hollow fiber, capillary tube, and the like. The expression includes also a material that erodes or is leached from wall 22 in the fluid environment of use to produce at least one passageway in dosage form 20. Representative materials suitable for forming at least one passageway, or a multiplicity of passageways include an erodible poly(-glycolic) or poly(lactic) acid member in the wall, a gelatinous filament, leachable materials such as removable pore forming polysaccharide, salt or oxide, and the like. A passageway or a plurality of passageways can be formed by leaching a material such as sorbitol from the wall to produce a controlled release pore-passageway. The passageway can be a microporous member as seen in FIG. 3. The microporous passageways comprising a microporous member can be performed or formed during operation of the dosage form. The passageways can have any shape such as round, elliptical, and the like. Passageways and equipments for forming passageways are disclosed in U.S. Pat. Nos. 3,916,899, 4,063,064; and 4,088,864. Passageways of controlled dimensions formed by leaching in osmotic systems are disclosed in U.S. Pat. No. 4,209,098.

Wall 22 of dosage form 20, and film 28 can be applied by using an air suspension procedure. This procedure consist in suspending and tumbling compressed drug 26, or osmagent 29 in a current of air using a wall forming composition unit wall 22 is applied around the compressed drug, or the film is applied around osmagent 29. The air suspension procedure is well-suited for the wall or the film. The air suspension procedure is described in U.S. Pat. No. 2,799,241; in J. Am. Pharm. Assoc., vol. 48, pages 451 to 459, 1959; and ibid, Vol. 49, pages 82 to 84, 1960. The wall, or the film forming composition can be applied with a Wurster ® air suspension coater, or an Aeromatic ® air suspension coater can be used for forming the wall or the film. Other techniques such as pan coating can be used for providing the dosage form. In the pan coating system, the wall forming composition are deposited by successive spraying of the composition accompanied by tumbling in a rotating pan. A pan coater is used to produce a thicker wall or film. Finally, the wall coated dosage form, or the film coated osmagent are dried in a forced air oven at 50° C. for a week, or in a temperature and humidity controlled oven, at 50° C. and 50 R.H., relative humidity, for 24 hours. Generally, the wall, or the film formed by these techniques have a thickness of 1 to 20 mils, and in a presently preferred embodiment of 2 to 10 mils.

Exemplary solvents for manufacturing the wall or the film include inert organic and organic solvents that do not adversely harm the wall, the film or the final dosage form. The solvents broadly include a member selected from the group consisting of an alcohol, ketone, ester, ether, aliphatic hydrocarbon, halogenated solvent, cycloaliphatic solvent, aromatic, heterocyclic, aqueous solvent, mixtures thereof, and the like.

The dosage form is manufactured by standard techniques. For example, in one manufacture the beneficial drug and the film coated osmagent are blended and pressed into a solid layer. The layer possesses dimensions that correspond to the internal dimensions of the area occupied in the dosage form. Optionally, the drug formulation and the film coated osmagent member can be blended with a solvent, mixed by conventional methods such as ballmilling, calendering, stirring, or rollmilling and then pressing into a preselected shape. The compressed compartment forming mass is then coated with an outer wall. The wall forming composition can be applied by press coating, molding, spraying, dipping or air suspension procedures. The air suspension and air tumbling procedures comprise suspending and tumbling the pressed composition until surrounded by the wall.

In another manufacture, the dosage form is made by wet granulation technique. In the wet granulation technique the drug is blended with other compartment forming ingredients using an organic cosolvent, such as isopropyl alcohol-methylene dichloride, 80/20, V/V (volume/volume), as the granulation fluid. The ingredients are passed through a 40 mesh screen and blended in a mixer. Then, the film coated osmagent moiety is added with continual mixing in the blender. The blend is dried for 18 to 24 hours at 40°-45° C. in a forced air oven. Next, a lubricant is added to the dry blend, and the newly formed mixture put into milling jars and mixed on a jar mill for 5 to 15 minutes. The composition is pressed into a layer in a Manesty ® layer press at a maximum load of 2 tons. The pressed mass is fed to a coater (pan coater or air suspension coater) and coated with an exterior wall.

Another manufacturing process that can be used for providing the compartment-forming composition comprises blending a powdered drug and other ingredients in a fluid bed granulator. After the powdered ingredients are dry blended in the granulator, a granulating fluid, for example, polyvinyl pyrrolidone in water, and film coated osmagent member, are added to the granulating fluid sprayed onto the powder and member. The coated powder and member then are dried in the granulator. After drying, a lubricant such as magnesium stearate is added to the granulator. The granules are then pressed in the manner described above.

DESCRIPTION OF EXAMPLES OF THE INVENTION

The following examples are merely illustrative of the present invention and they should not be considered as limiting the scope of the invention in anyway, as these examples and other equivalents thereof will become more apparent to those versed in the dispensing art in the light of the present disclosure, the drawing figures, and the accompanying claims.

EXAMPLE 1

A dosage form is manufactured for delivering a beneficial drug as follows: first 950 g of aspirin powder, 50 mesh size, is granulated in an Aeromatic ® fluid bed granulator. The granulating fluid consists of 50 g of hydroxypropylmethyl cellulose dissolved in 760 g of methylene chloride: 190 g of methanol. The granules are dried in a forced air oven at 50° C. for 4 hrs.

Next, 850 g of anhydrous sodium acetate crystalline powder is granulated in the fluid bed granulator. The granulating fluid consists of the following: hydroxypropylmethyl cellulose 6 g; cellulose acetate 39.8% acetyl content 9 g; both dissolved in methylene chloride 228 g—methanol 57 g. The granules are dried in a forced air oven for 10 hrs at 50° C.

Then, 600 g of aspirin granules and 400 g of the sodium acetate granules, and 15 g of magnesium stearate are blended together in a V-blender for seven minutes. The granules thus obtained were transferred to a Manesty ® tablet press. The press consists of seventeenth inch oval dies and mated punches. A series of 932 mg oval shaped tablets are compressed with the press. The aspirin content is about 500 mg for each pressed mass.

Next, the following ingredients are blended together using a methylene chloride and methanol solvent system: cellulose acetate with a 39.8 acetyl content, 50 wt %; cellulose with a 32% acetyl content 50 wt %; methylene chloride 85 wt %; and methanol 15 wt %. The coating solution is used in a Wurster ® coater, for air suspension coating a 50 mg wall around each compressed mass. The dosage forms are dried in a forced air oven for 2 days at 45° C. to remove the coating solvent.

Figure 4:
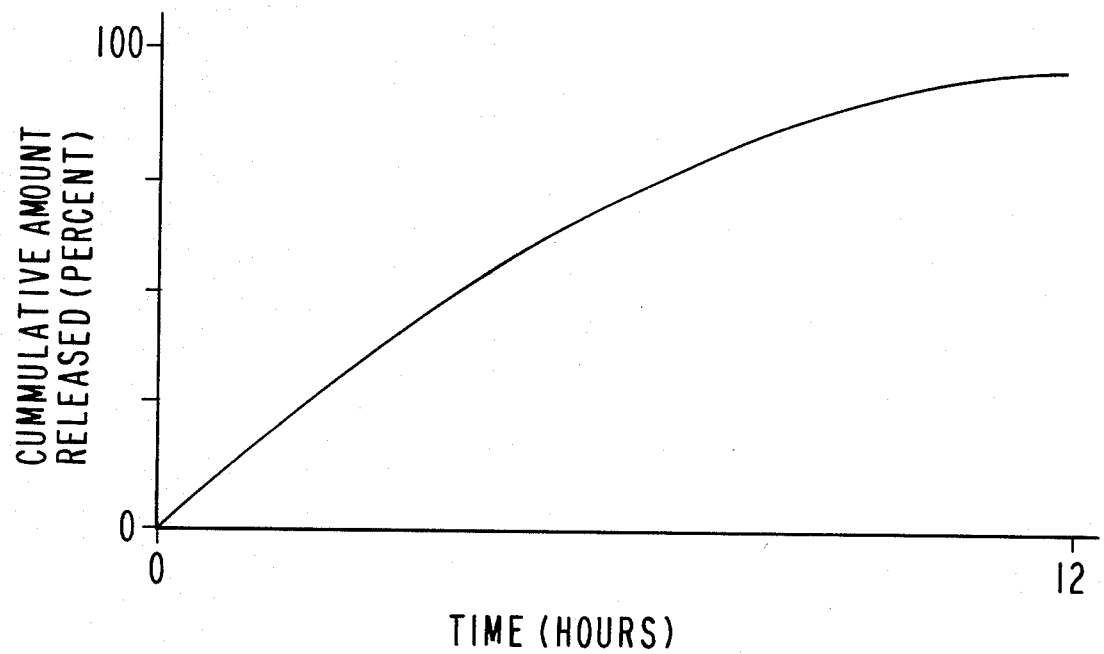
Figure 5:
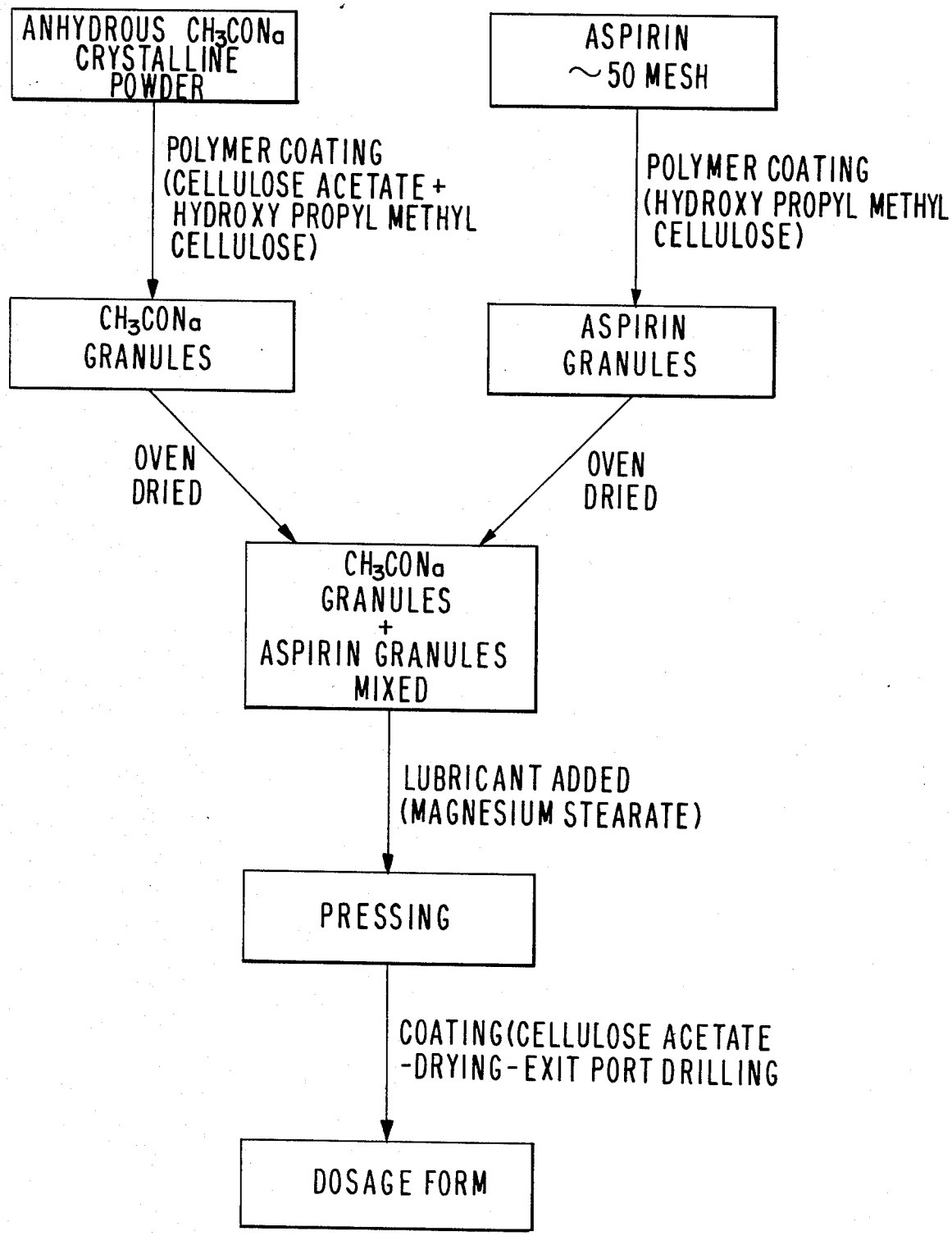

Finally, a 0.51 mm exit passageway is drilled through the wall for releasing the aspirin form the dosage form. The release rate of aspirin from the dosage form is plotted in FIG. 4. In FIG. 5, a flow diagram is set forth to illustrate the process used for manufacturing the dosage form.

EXAMPLE 2

The procedure described above is repeated with the added condition consisting in coating anhydrous, crystalline powder sodium acetate, and aspirin with acrylic polymer to yield a dosage form comprising a wall consisting of 50 wt % cellulose acetate having an acetyl content of 32%, and 50 wt % cellulose acetate having an acetyl content of 39.8%, which wall surrounds a compartment comprising polyacrylic coated aspirin 48.5%, polyacrylic coated sodium acetate 45 wt %, and 6.5 magnesium stearate. The dosage form had a single 0.51 mm passageway.

In summary, it will be readily appreciated that the present invention contributes ot the art an unobvious dosage form manufactured as a drug delivery device possessing wide and practical applications. While the invention has been described and pointed out in detail and with reference to operative embodiment thereof, it will be appreciated that those skilled in the art will appreciate that various changes, modifications, substitutions and omissions can be made without departing from the spirit of the invention. It is intended, therefore, that this invention embrace those equivalents within the scope of the invention disclosed and claimed.

We claim:

1. A dosage form for delivering a beneficial drug formulation to a biological environment of use, wherein the dosage form comprises:
   (a) a wall comprising a composition that maintains its physical and chemical integrity during the life of the dosage form, is substantially impermeable to the passage of a beneficial agent formulation, and at least in part is permeable to the passage of exterior fluid present in the biological environment, which wall surrounds and forms;
   (b) a compartment;
   (c) a dosage amount of a beneficial drug formulation in the compartment;
   (d) means for aiding in controlling the solubility of the drug formulation in the presence of external fluid imbibed into the compartment, said means comprising a release rate controlling film selected from the group consisting of olefin and vinyl polymers, condensation polymers, addition polymers and organo-silicon polymers, which film surrounds a buffer that is released at a controlled rate by the film into the compartment for governing the solubility of the drug formulation and correspondingly aiding in osmotically and hydrodynamically delivering the drug formulation from the dosage form; and,
   (e) exit means in the wall of the dosage form that connects the internal compartment with the exterior environment of use for delivering the drug formulation in a therapeutically effective amount from the dosage form.

2. A dosage form for delivering a beneficial drug formulation to an environment of use, the dosage form comprising:
   (a) a wall comprising a composition that maintains its physical and chemical integrity during the life of the dosage form, is substantially impermeable to the passage of a drug formulation, and at least in part is permeable to the passage of exterior fluid, which wall surrounds and defines;
   (b) a compartment;
   (c) a dosage amount of a beneficial drug formulation in the compartment;
   (d) means for governing the solubility of the drug formulation in the compartment in the presence of fluid imbibed into the compartment, said means comprising a release rate controlling film selected from the goup consisting of olefin and vinyl polymers, condensation polymers, addition polymers and organo-silicon polymers, which film surrounds an osmagent that is released at a controlled rate into the compartment by the film for governing the solubility of the drug formulation in the compartment and for correspondingly aiding in osmotically and hydrodynamically delivering the drug formulation from the doage form; and,
   (e) exit means in the wall of the dosage form that connects the compartment with the exterior of the dosage form for delivering the drug formulation from the dosage form.

3. The dosage form for delivering a beneficial drug formulation according to claim 2, wherein the exit means is formed in the wall when the dosage form is in the environment of use by fluid leaching a leachable compound from the wall.

4. The dosage form for delivering a beneficial drug formulation according to claim 2, wherein the exit means comprises at least one pore of controlled porosity for delivering the drug formulation from the dosage form.

5. The dosage form for delivering a beneficial drug formulation according to claim 2, wherein the exit means comprises a plurality of micropores.

* * * * *